US012799052B2

United States Patent

(12) United States Patent
Paul et al.

(10) Patent No.: US 12,799,052 B2
(45) Date of Patent: Nov. 17, 2026

(54) ENERGY-EFFICIENT DISTILLATION PROCESS WITH VARIATION OF INFLOW

(71) Applicant: Evonik Oxeno GmbH & Co. KG, Marl (DE)

(72) Inventors: Niklas Paul, Marl (DE); Armin Matthias Rix, Marl (DE); Tanita Valèrie Six, Dortmund (DE); Tanja Steenweg, Dortmund (DE); Lea Wessner, Dortmund (DE); Martin Oldemeyer, Haltern am See (DE)

(73) Assignee: Evonik Oxeno GmbH & Co. KG, Marl (DE)

( * ) Notice: Subject to any disclaimer, the term of this patent is extended or adjusted under 35 U.S.C. 154(b) by 151 days.

(21) Appl. No.: 18/958,187

(22) Filed: Nov. 25, 2024

(65) Prior Publication Data

US 2025/0171386 A1 May 29, 2025

(30) Foreign Application Priority Data

Nov. 29, 2023 (EP) .................................... 23213043

(51) Int. Cl.
*C07C 7/04* (2006.01)
*C07C 7/00* (2006.01)
*G01J 3/44* (2006.01)
*G01N 30/02* (2006.01)

(52) U.S. Cl.
CPC ................ *C07C 7/04* (2013.01); *C07C 7/005* (2013.01); *G01J 3/44* (2013.01); *G01N 30/02* (2013.01); *G01N 2030/025* (2013.01)

(58) Field of Classification Search
CPC ... C07C 7/04; C07C 7/005; G01J 3/44; G01N 30/02; G01N 2030/025; B01D 3/143; B01D 3/4294; B01D 3/00; B01D 3/008; C10G 7/12
See application file for complete search history.

(56) References Cited

U.S. PATENT DOCUMENTS 1,957,818 A * 5/1934 Carney .......................... 195/11
3,230,154 A * 1/1966 Walker ........................... 203/40

* cited by examiner

*Primary Examiner* — Prem C Singh
(74) *Attorney, Agent, or Firm* — Grüneberg Global IP, PLLC

(57) ABSTRACT

A process for distilling a raffinate 2 stream as feed stream in at least two distillation columns DK1 and DK2 has two different inlets for the feed stream in at least the distillation column DK1. It is a feature of the process that the feed stream is analysed for its composition before being introduced; and one of the at least two inlets for the feeding of the feed stream is chosen depending on the composition of the feed stream.

18 Claims, 9 Drawing Sheets

ENERGY-EFFICIENT DISTILLATION PROCESS WITH VARIATION OF INFLOW

CROSS-REFERENCE TO RELATED APPLICATIONS

This patent application claims priority to European Patent Application No. 23213043.5, filed on Nov. 29, 2023, in the European Patent Office, the entire disclosure of which is hereby incorporated by reference herein.

BACKGROUND OF THE INVENTION

Field of the Invention

The present invention relates to a process for distilling a raffinate 2 stream as feed stream in at least two distillation columns DK1 and DK2, wherein at least distillation column DK1 has two different inlets for the feed stream. It is a feature of the process that the feed stream is analysed for its composition before being introduced; and one of the at least two inlets for the feeding of the feed stream is chosen depending on the composition of the feed stream.

Description of Related Art

The distillation of hydrocarbon streams is a proven technique for separating substances from substance mixtures. Distillation processes are therefore indispensable in the chemical industry in the production of many chemical substances. Examples of these are the distillation of feed streams for removal of low- or high-boiling components before a chemical reaction, or the distillation of crude product mixtures for removal of reactants and low- and/or high-boiling by-products.

The hydrocarbon streams used in distillation are generally subject to natural and/or production-related fluctuations in composition. This means that the proportions of the components in the hydrocarbon streams become greater or smaller, new components are introduced and/or other components disappear. These include, for example, streams of matter in petrochemical production plants. These hydrocarbon streams are especially C4 hydrocarbon streams from steamcrackers, FCC C4 streams, product streams from MTBE synthesis (MTBE=methyl tert-butyl ether), raffinate 2 streams or product streams from oligomerization.

C4 hydrocarbon streams consist essentially of butadiene, isobutene, 1-butene, the two 2-butenes, isobutane and n-butane. Customary workup methods that are implemented globally for such C4 hydrocarbon streams comprise the following steps: first the majority of the butadiene is removed. In both cases this leaves a hydrocarbon mixture which, as well as the saturated hydrocarbons n-butane and isobutane, contains the olefins isobutene, 1-butene and 2-butenes, and is referred to as raffinate 1. One possible way of removing the isobutene from this mixture is reaction with methanol to give MTBE. This leaves the saturated hydrocarbons, linear butenes and possibly a residual amount of isobutene. The mixture obtained after removal of the butadiene and isobutene is referred to as raffinate 2.

Fluctuating compositions of the proportions of the individual components in the hydrocarbon streams and in particular in the raffinate 2 can have the effect that the separation task can no longer be adequately accomplished, or higher amounts of energy have to be used for accomplishment of the separation task.

SUMMARY OF THE INVENTION

The problem addressed by the present invention was therefore that of improving known distillation processes. Fluctuating compositions of the proportions of the components in the raffinate 2 were to be absorbed with a minimum level of complexity, while the separation task is accomplished in a very substantially uniform manner.

DETAILED DESCRIPTION OF THE INVENTION

Figure 1:
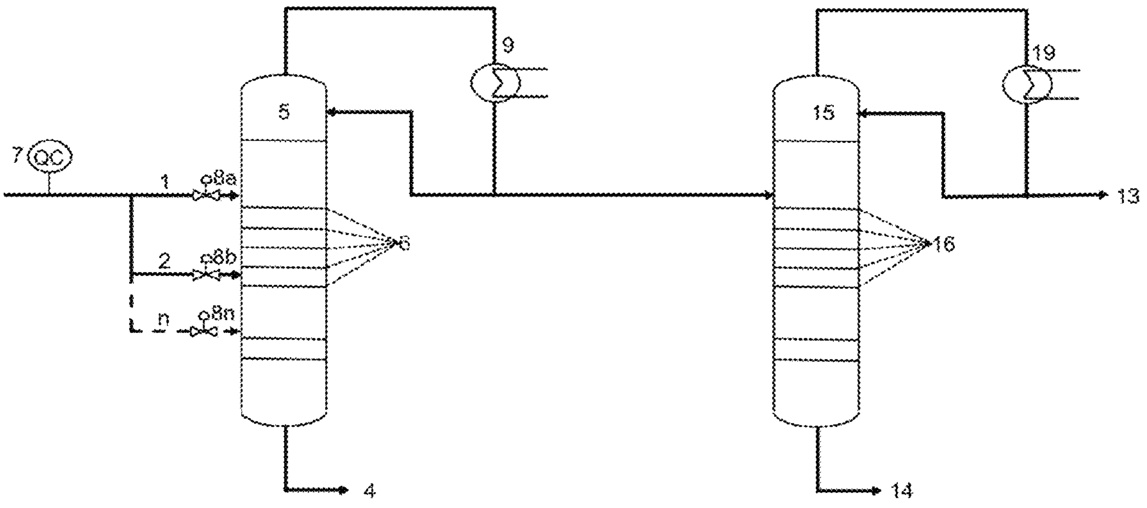
FIG. 1 shows a configuration with two distillation columns DK1 (5) and DK2 (15) having a multitude of internals (6, 16).

This problem is solved by the embodiment of the process proposed in the description herein. Preferred embodiments are also specified in the dependent embodiments. The process according to the invention is a process for distilling a raffinate 2 stream as feed stream in a separation unit comprising at least two distillation columns DK1 and DK2, wherein

- distillation columns DK1 and DK2 each comprise a top at the upper end of the column and a bottom at the lower end of the column, where a vapour stream is obtained at the top and a bottom stream at the bottom in each case, and where distillation column DK2 is fed with a portion of the vapour stream from DK2;
- the vapour streams from DK1 and DK2 are at least partly condensed, and the condensation energy obtained from at least one of the vapour streams from DK1 or DK2 is used by means of vapour compression or by means of a heat pump for heating of at least one of distillation columns DK1 and DK2;

at least distillation column DK1 has at least two different inlets for the feed stream, where the inlets, viewed from the top of the distillation column, are arranged one below another;

the feed stream is analysed for its composition before being introduced; and one of the at least two inlets for the supply of the feed stream is chosen depending on the composition of the feed stream.

One advantage of the process according to the invention is that the choice of a suitable inlet into the distillation column results in optimized separation of the hydrocarbon stream used and of the raffinate 2 stream, and simultaneous saving of energy.

The feed stream which is fed into the distillation according to the invention is a hydrocarbon stream. The feed stream used in the distillation process according to the invention is a raffinate 2 stream. A raffinate 2 stream contains at least 1-butene, 2-butene, n-butane and isobutane. Raffinate 2 streams may be subjected to removal of 1-butene later on in the integrated petrochemical processes. This involves separating 1-butene from the raffinate 2 by distillation, giving a raffinate 3. This removal of 1-butene is preferably conducted by the distillation process according to the invention. The removal of 1-butene is incidentally generally not conducted in full. It is thus possible for 1-butene to remain in the raffinate 3.

The hydrocarbon stream used in the distillation process according to the invention is a raffinate 2 stream containing at least 1-butene, 2-butene, n-butane and isobutane. The 1-butene would be at least partly separated from raffinate 2 streams in the distillation.

The raffinate 2 used preferably contains less than 2500 ppm, preferably less than 1000 ppm, more preferably less than 500 ppm, of isobutene. Further preferably, the raffinate 2 used in the process of the present invention contains less than 4% by weight of polyunsaturated C4 hydrocarbons. In a particularly preferred embodiment, the concentration of the polyunsaturated C4 hydrocarbons should be less than 500 ppm. If the streams should contain higher amounts of butadiene, it would be possible to conduct a selective hydrogenation beforehand, in which the butadiene is converted to butenes and/or butanes. Corresponding processes are known to those skilled in the art.

The raffinate 2 stream used may additionally contain certain amounts of water, especially in an amount of 150 to 4000 ppm. It is preferable that the water is at least partly removed by the distillation. The water will accumulate in the vapour stream obtained in the distillation column and be obtained as a second liquid phase after condensation, which can be separated off via udders in the distillate vessels of the distillation column. The bottom product from the distillation column features very low contents of butadiene and water, preferably each below 100 ppm, more preferably below 5 ppm.

The process according to the invention is conducted in a separation unit comprising at least two distillation columns DK1 and DK2. The distillation columns may be any known distillation column suitable for the corresponding separation process. Distillation columns DK1 and DK2 are constructed such that they each comprise a top at the upper end of the column and a bottom at the lower end of the column. At least the distillation column DK1 has at least two different inlets via which the feed stream used, i.e. the raffinate 2, can enter the distillation column DK1. The at least two inlets, viewed from the top of the column, i.e. from the upper end of the column, are arranged one below another. The at least two inlets are thus not disposed at the same height but at a different height, viewed spatially and from the bottom. It is also possible that distillation column DK2 has at least two different inlets via which the stream from DK1 can enter distillation column DK2.

It will be apparent that the distillation column DK1 or DK2 for the process according to the invention may also have more than two, i.e. three, four, five or more, inlets via which the respective stream is directed into the distillation column according to its composition.

The thermal energy required for the separation task is typically introduced into distillation columns via at least one reboiler. A stream preferably flows here through the reboiler, which is withdrawn at the lower end, i.e. in or at the bottom of the distillation column and, after passing through the reboiler, is returned back to the distillation column. The stream is heated as it passes through the reboiler.

According to the invention, "reboilers" refer to evaporators that heat the bottom of the respective distillation column. Such a reboiler is typically disposed outside the respective distillation column. Since reboilers transfer energy, in particular heat, from one stream to another, they are heat transferrers. The stream to be evaporated is (at least partly) drawn off from the bottom of the distillation column via a draw and fed to the reboiler. The evaporated stream, with or without a residual proportion of liquid, is returned back to the respective distillation column in the region of the bottom via at least one feed.

Suitable evaporators that can be used as reboilers are, for example, natural circulation evaporators, forced circulation evaporators, forced circulation flash evaporators, kettle evaporators, falling-film evaporators or thin-film evaporators. Heat exchangers for the evaporator that are typically used in the case of natural circulation evaporators and forced circulation evaporators are a shell-and-tube or plate apparatus. As well as those mentioned, it is alternatively possible to use any other design of evaporator which is known to those skilled in the art and is suitable for use in a distillation column.

The at least two distillation columns preferably also have a multitude of internals, such as random packings, structured packings or trays. These internals ensure that the vapour ascending within the distillation column and the liquid flowing down are sufficiently contacted and improve mass transfer and heat transfer. Trays used are typically bubble-cap trays, sieve trays, valve trays having fixed or movable valves, tunnel-cap trays or slotted trays. Unstructured packings are generally beds of random packings. Random packings used are typically Raschig rings, Pall rings, Berl saddles, Super-Rings/Super-Rings Plus or Intalox® saddles. Structured packings are sold for example under the Mellapak® trade name by Sulzer. These and other suitable internals are known to a person skilled in the art and can likewise be used.

Preferred internals have a low specific pressure drop per theoretical plate. Structured packings and random packing elements have, for example, a significantly lower pressure drop per theoretical plate than trays. This has the advantage that the pressure drop in the distillation column(s) remains as low as possible and hence the mechanical output of the compressor and the temperature of the raffinate 2 stream to be evaporated remains low.

In a particularly preferred embodiment of the present invention, distillation column DK1 comprises internals, preferably between 2 and 300 internals, further preferably between 2 and 250 internals, more preferably 2 to 220 internals. The internals are arranged one below another within the distillation column DK1, viewed from the top of the distillation column. In a preferred embodiment of the present invention, the inlets are each at the height of at least one of the internals. Since the inlets are arranged one below another, the inlets may in principle also be disposed at a different height based on one of the internals. However, it is particularly preferable that the at least two inlets are at the height of different internals.

In an additionally particularly preferred embodiment of the present invention, distillation column DK2 comprises internals, preferably between 2 and 300 internals, further preferably between 2 and 250 internals, more preferably 2 to 220 internals. The internals are arranged one below another within the distillation column DK2, viewed from the top of the distillation column. In a preferred embodiment of the present invention, the inlets are each at the height of at least one of the internals. Since the inlets are arranged one below another, the inlets may in principle also be disposed at a different height based on one of the internals. However, it is particularly preferable that the at least two internals are at the height of different internals.

The internals in distillation columns are defined by the theoretical plates that they generate. Distillation columns are generally designed via the number of theoretical plates. In the case of trays as internals, the number of theoretical plates is found by multiplication by the tray efficiency (number of theoretical plates=number of trays*tray efficiency). In the case of random packings or structured packings, the number of theoretical plates is found via the HETP value (height equivalent for one theoretical plate) by multiplication by the height of the bed of random packings or structured packing used (number of theoretical plates=HETP value*height of bed of random packings or structured packing). The HETP value can be determined with reference to the substance mixture to be separated and the random packing or structured packing used. Typically, multiple theoretical plates result from a random packing or a structured packing, i.e. one of the internals.

It should be clear that the separation unit may comprise one or more further distillation columns. Whether there are one or more further distillation column(s) in the separation unit depends on the separation task to be accomplished. If fluctuations in the feed composition are also to be expected in the stream to the further distillation column(s), variation of the inlet chosen would also be applicable here with reference to the composition of the respective stream. The one or more distillation column(s) may likewise be constructed like the distillation column already described, i.e. have a bottom and a top, may utilize a reboiler for introduction of the thermal energy and may comprise a multitude of internals such as random packings, structured packings or trays.

The first step in the process according to the invention is that the feed stream, i.e. the raffinate 2, is analysed for its composition before being introduced. This means that at least the (percentage) proportions, concentrations or amounts of the component(s) of the raffinate 2 stream that are of relevance for the choice of inlet for the feeding of the hydrocarbon stream are determined. In a preferred embodiment, in each case, the components of the characteristic separations are determined; in the present case, for use of a raffinate 2 stream, it is preferable that the n-butane content and/or the isobutane content are determined. The analysis of the composition can be conducted by any known analysis methods. Preferred analysis methods for the process according to the invention are Raman spectroscopy and gas chromatography. The composition of the raffinate 2 stream can in principle be analysed online, i.e. such that the measurement is effected within the process. On the other hand, the measurement can also be effected such that a sample is taken at a suitable point and this sample is then analysed outside the process.

Depending on the composition of the raffinate 2 stream or of the stream fed to DK2, one of the at least two inlets for the feeding of the respective stream is then chosen. This means that either the higher or lower inlet of the at least two inlets—based on the at least two inlets—functions as feed for the distillation column via which the respective stream, i.e. for example the raffinate 2 stream, is directed into the distillation column. This applies correspondingly if there are more than two inlets, although it is not necessarily the case that the highest or lowest inlet must be chosen, but also the inlet(s) in between.

The pipelines to the at least two inlets of the distillation column in the distillation according to the invention preferably have separate closure devices in order to be able to independently close and open the pipeline to each inlet. Corresponding closure devices are familiar to the person skilled in the art, for example suitable types of valves.

The process according to the invention may in principle be operated continuously or in batchwise mode. The process according to the invention is preferably a continuously operated process.

Both in the case of continuously operated processes and in the case of processes operated in batchwise mode, the composition of the stream used may change during the process. Industrially used material streams, here the raffinate 2, are regularly subject to certain fluctuations. This change in composition is not always so great that it affects the distillation process in question. But it is also possible that, during the process according to the invention, the composition of the respective stream changes and therefore has to be switched over to another inlet. This means that the composition of the stream used in each case is analysed not just once but continuously at predefined time intervals throughout the process. The separation between two analysis measurements may be varied depending on the type of hydrocarbon stream used. In principle, there may be 10 to 59 seconds, 1 to 59 minutes, 1 to 23 hours or 1 to several days between two analysis measurements.

If a changeover from one to another of the at least two inlets is required, the changeover of the respective stream to another inlet may be automatic or manual. In the changeover, one inlet and/or the conduit to the inlet is closed and the other inlet and/or the conduit to the inlet is opened.

If the changeover to another inlet is automatic, the changeover can be effected such that the analysis results are evaluated by means of a control unit, for example by means of a computer, and, in the event that a value goes above or below a limit in the composition of the respective stream, the changeover to another inlet is made. Such automation with the aid of computer-assisted evaluation is quite easy to implement since it is a comparison between limit value and measurement. In addition, human error is avoided as far as possible, and the changeover can be made more quickly. Suitable limits are all measurable parameters associated with the composition of the stream or its components, i.e., for example, the already mentioned (percentage) proportions, concentrations or amounts of the component(s) in the stream.

It is preferable in the context of the present process when at least one of the two distillation columns DK1 and DK2 is operated with reflux; preferably, both distillation columns DK1 and DK2 are operated with reflux. What is meant by "reflux" is that the vapour stream withdrawn at the top end of the distillation column is at least partly conducted back to the at least one distillation column. A reflux can be established by mounting a condenser at the top of the respective distillation column. The vapour stream is at least partly condensed in the condenser and fed back to the distillation column. In the cases where such a reflux is established, the reflux ratio is preferably less than 1 to 100, further preferably 1 to 50, especially preferably 1 to 30. Generally and in the context of the present invention, a reflux ratio is understood to mean the ratio of the proportion of the mass flow withdrawn from the column (kg/h) that is recycled into the column in liquid form (reflux) to the proportion of this mass flow (kg/h) that is discharged from the respective column in liquid form or gaseous form.

The temperature and pressure in the at least one distillation column are determined by the desired separation task and hence with reference to the hydrocarbon stream used. The discovery of the correct temperature and the correct pressure is not a problem to the person skilled in the art. The person skilled in the art will be able to determine temperature and pressure quite easily from the relative volatility or with reference to the separation task to be accomplished.

Distillation processes are generally quite energy-intensive processes in which thermal energy is introduced via the bottom in order to accomplish the separation task. At the same time, the vapour removed is cooled in order to at least partly condense it. It is advantageous in the process according to the invention to take thermal integration measures in order to recover energy within the system and to render it utilizable. Suitable measures for thermal integration are vapour compression and the use of a heat pump.

One possible measure for thermal integration is vapour compression. This involves at least partial compression of the vapour stream withdrawn at the top. This increases the pressure of the vapour stream. The compression introduces additional energy into the system. The compression of at least a portion of the vapour stream can be effected in any manner known to the person skilled in the art. For example, the compression can be performed mechanically and in a single-stage or multistage compression. What is meant by "single-stage" in this connection is that compression takes place from one pressure level to another. What is meant by "multistage" is that compression is effected first to a pressure level X and then from X to the pressure level Y. In a multistage compression, it is possible to use two or more compressors of the same type or compressors of different types. A multistage compression can preferably be effected with one compressor machine or with multiple compressor machines. The use of single-stage compression or multistage compression depends on the compression ratio and hence on the pressure to which the vapour substream is to be compressed.

A suitable compressor in the process according to the invention, especially for compression of the vapour stream, is any compressor known to the person skilled in the art, preferably mechanical compressor, with which gas streams can be compressed. Suitable compressors are, for example, single-stage or multistage geared turbocompressors, piston compressors, screw compressors, centrifugal compressors or axial compressors.

After the compression, the compressed vapour stream is conducted to a heat exchanger, where it transfers thermal energy to another stream. It would be possible, for example, to transfer thermal energy to the stream in the reboiler and hence to heat the distillation column. According to the invention, the phrase "transfer of energy" especially means "heating", i.e. transfer of energy in the form of heat.

Another measure for thermal integration is the use of a heat pump. The vapour stream withdrawn at the top of the at least one distillation column is used here to transfer thermal energy to a heat transfer medium. After the transfer of energy, the heat transfer medium preferably has an elevated temperature and/or an elevated pressure.

The transfer of energy can be performed by methods known to the person skilled in the art or with heat exchangers known to the person skilled in the art. Suitable evaporators that can be used as heat exchangers are, for example, natural circulation evaporators, forced circulation evaporators, forced circulation flash evaporators, kettle evaporators, falling-film evaporators or thin-film evaporators. As well as those mentioned, it is alternatively possible to use any other design of evaporator which is known to those skilled in the art and is suitable for use in a distillation column. The heat exchanger in this case may also be the condenser for condensation of the vapour stream. This has the advantage that there is no need to install an additional condenser.

The heat transfer medium utilized may be any working medium familiar to the person skilled in the art. The heat transfer medium is preferably selected from the group consisting of water; alcohols; alcohol-water mixtures, salt-water solutions; ammonia; mineral oils, for example diesel oils; thermal oils, for example silicone oils; biological oils, for example limonene; and aromatic or aliphatic hydrocarbons, for example dibenzyltoluene, further preferably water, methanol, ethanol, propanol, n-pentane, n-butane, n-hexane, n-propane or ammonia, especially preferably water.

After the energy transfer mentioned, the heat transfer medium is at least partly compressed, giving rise to a compressed heat transfer medium at a higher pressure than the heat transfer medium prior to the compression.

The compressing of the at least one portion of the heat transfer medium can be effected in any manner known to the person skilled in the art. For example, the compression, as already defined above, can be performed mechanically and in a single-stage or multistage compression. A suitable compressor in the process according to the invention is any compressor known to the person skilled in the art, preferably mechanical compressor, with which gas streams can be compressed. Suitable compressors are, for example, single-stage or multistage geared turbocompressors, piston compressors, screw compressors, centrifugal compressors or axial compressors.

In the next step, energy is transferred from the compressed heat transfer medium to a stream to be heated in the system, preferably in the reboiler, in order to heat a distillation column thereby.

By contrast with the vapour compression, in which the vapour obtained at the top of the distillation column is compressed and used for transfer of thermal energy, there is thus an intervening heat transfer medium when a heat pump is used. However, the principle is the same: energy is collected at one point in the process and used at another point in the process.

The present process is used for the separation of a raffinate 2 stream. The separation unit here preferably consists of at least two distillation columns DK1 and DK2, where the at least two different inlets for the hydrocarbon stream are in the first distillation column DK1. The raffinate 2 which is directed to the first distillation column DK1 is separated in distillation column DK1 into at least two streams, i.e. at least one vapour stream BS1 which comprises at least 1-butene and isobutane and is withdrawn at the top of DK1, and at least one bottom stream which comprises at least 1-butene and 2-butene and is withdrawn at the bottom of DK1. The vapour stream BS1 can also be withdrawn at the top of the distillation column in the form of multiple substreams BS1(n) where n is an integer and is equal to the number of substreams. The same also applies to the bottom stream. The temperature at the bottom of the first distillation column DK1 is preferably in the range from 40 to 110 °C, preferably 50 to 100 °C.

The pressure and temperature of the vapour stream BS1 are specified hereinafter. This relates in particular to the pressure and temperature of the at least one vapour stream BS1 when it is withdrawn from distillation column DK1. The pressure of the vapour stream BS1 is especially in the range from 6 to 15 bar absolute, preferably in the range from 7.5 to 13 bar absolute. The temperature of the vapour stream BS1 is especially in the range from 45 °C to 120 °C, preferably in the range from 48 °C to 100 °C, further preferably in the range from 50 °C to 90 °C, further preferably in the range from 55 °C to 80 °C, more preferably in the range from 60 °C to 80 °C.

What is meant in the context of the present invention by the withdrawal of the at least one vapour stream BS1 comprising at least 1-butene and isobutane at the top of distillation column DK1 is in particular that the at least one vapour stream BS1 is withdrawn as top stream or as side draw above the internals in distillation column DK1.

What is meant in the context of the present invention by the withdrawal of the at least one bottom stream comprising at least 1-butene and 2-butene at the bottom of distillation column DK1 is in particular that the at least one bottom stream is withdrawn directly at the bottom or at the lower tray of distillation column DK1.

Distillation column DK1 is preferably operated with reflux. What is meant by "reflux" is that the vapour stream BS1 withdrawn at the top end of distillation column DK1 is at least partly fed back to distillation column DK1. In the cases where such a reflux is established, the reflux ratio is preferably 2 to 30, more preferably 5 to 20, especially preferably 8 to 15.

The vapour stream from the first distillation column DK1 is conducted to the second distillation column DK2. Thermal integration measures such as vapour compression or the use of a heat pump are possible here, where energy can be collected by at least partial condensation of the vapour stream BS1 and used for heating of DK1 and/or DK2. If the amounts of isobutene in the stream conducted to distillation column DK2 are too high to meet the specification for the 1-butene product from DK2, it is possible for an additional MTBE or ETBE synthesis to be disposed between distillation columns DK1 and DK2. For this purpose, the stream is conducted to an MTBE or ETBE synthesis, isobutene present is at least partly converted to MTBE or ETBE, and then the MTBE or ETBE formed is separated off.

MTBE or ETBE synthesis is known in principle to those skilled in the art. For the preparation of MTBE or ETBE from isobutene-containing streams, it is possible in particular to use acidic ion exchange resins (sulfo groups) as heterogeneous catalysts. The MTBE or ETBE synthesis may take place in one or more series-connected reactors. The catalyst is preferably used in the form of a fixed bed catalyst. Since the formation of MTBE or ETBE is an equilibrium reaction, it may be appropriate to use at least one reactive distillation column in which the reaction and removal of the MTBE or ETBE are simultaneous. In the reactive distillation, the pressure should be in the range from 3 to 15 bar and the temperature in the reaction zone from 55 to 75 °C. After the synthesis, MTBE or ETBE is separated off, preferably by distillation. This method is also known to the person skilled in the art. The stream which is then obtained, which contains less isobutene, can then be conducted to distillation column DK2.

In the second distillation column DK2, the hydrocarbon stream supplied, here the vapour stream from DK1 that comprises at least isobutane and 1-butene, is separated into at least one vapour stream BS2 which comprises at least isobutane and is withdrawn at the top of DK2, and at least one product stream which comprises at least 1-butene and is withdrawn at the bottom of DK2. Distillation column DK2 may likewise have at least two different inlets for the hydrocarbon stream to be fed in from DK1, where the inlets, viewed from the top of distillation column DK2, are arranged one below another.

The distillation column DK2 used for the separation of the raffinate 2 stream may be any distillation column known to the person skilled in the art. Distillation column DK2 preferably contains internals. Suitable internals are for example trays, unstructured packings (random packings) or structured packings. Trays used are typically bubble-cap trays, sieve trays, valve trays having fixed or movable valves, tunnel-cap trays or slotted trays. Unstructured packings are generally beds of random packings. Random packings used are typically Raschig rings, Pall rings, Berl saddles, Super-Rings/Super-Rings Plus or Intalox® saddles. Structured packings are sold for example under the Mellapak® trade name by Sulzer. In addition to the internals mentioned, further suitable internals are known to those skilled in the art and may likewise be used.

Preferred internals have a low specific pressure drop per theoretical plate. Structured packings and random packing elements have, for example, a significantly lower pressure drop per theoretical plate than trays. This has the advantage that the pressure drop in distillation column DK2 remains as low as possible and hence the mechanical output of the compressor and the temperature of the stream to be evaporated remains low.

In a particularly preferred embodiment of the present invention, the second distillation column DK2 comprises a multitude of trays, preferably between 150 and 300 trays, further preferably between 170 and 220 trays.

What is meant in the context of the present invention by the withdrawal of the at least one vapour stream BS2 comprising at least isobutane at the top of distillation column DK2 is in particular that the at least one vapour stream BS2 is withdrawn as top stream or as side draw above the internals in distillation column DK2.

What is meant in the context of the present invention by the withdrawal of the at least one product stream comprising at least 1-butene at the bottom of distillation column DK2 is in particular that the at least one product stream is withdrawn directly at the bottom or at the lower tray of distillation column DK2. The product stream preferably contains at least 99% by weight of 1-butene, further preferably at least 99.5% by weight of 1-butene, more preferably at least 99.6% by weight of 1-butene. The 1-butene is the target product of the present process, and therefore the product stream is discharged from the process. The 1-butene may be used, for example, as a comonomer in the production of polyethylene.

The temperature at the bottom of the second distillation column DK2 during the process according to the invention is preferably in the range from 30 to 100 °C, preferably 45 to 80 °C. Further preferably, the pressure at the top of the second distillation column DK2 is in the range from 3 to 12 bar absolute, preferably 5 to 10 bar absolute.

Distillation column DK2 can also be operated with reflux. What is meant by "reflux" is that the vapour stream BS2 withdrawn at the top end of distillation column DK2 is at least partly fed back to distillation column DK2. In the cases where such a reflux is established, the reflux ratio is preferably 10 to 100, especially preferably 30 to 50.

The present invention is elucidated hereinafter with reference to figures. The figures serve for illustration, but should not be considered to be limiting.

FIG. 1 shows an embodiment with two distillation columns DK1 (5) and DK2 (15) having a multitude of internals (6, 16). The internals (6, 16) are shown merely schematically; in other words, the structure may differ in reality. Moreover, the number is often much higher in industrial practice. The internals (6, 16) are arranged one below another from the top of the column. In the present case, the internals are trays. The raffinate 2 to be separated can be directed into the distillation column DK1 (5) via conduit 1, conduit 2 or an optionally additional conduit n or via the corresponding inlets. The dotted conduit n indicates that there may be further inlets. Which of these conduits should be chosen is determined by analysis of the raffinate 2 via the corresponding analysis unit QC (7). The feeding of the raffinate 2 via one of the inlets (1, 2, n) is adjusted with the aid of valves (8*a*, 8*b*, 8*n*). The bottom stream (4) is removed at the bottom of column DK1 (5). The vapour stream is obtained at the top and is condensed in the heat exchanger (9). A portion of the condensed vapour stream is introduced into the first distillation column DK1 (5), and another portion into the second distillation column DK2 (15). A further distillation takes place therein. The bottom stream (14) is removed at the bottom of column DK2 (15). The vapour stream is obtained at the top and is condensed in the further heat exchanger (19). A portion of the condensed vapour stream is introduced into the first distillation column DK2 (15) and another portion is discharged. The thermal integration in which the condensation energy obtained in the heat exchangers (9, 19) is then used for heating of one or both bottoms of distillation columns DK1 and DK2 (5, 15), which is not shown in the figure.

Figure 2:
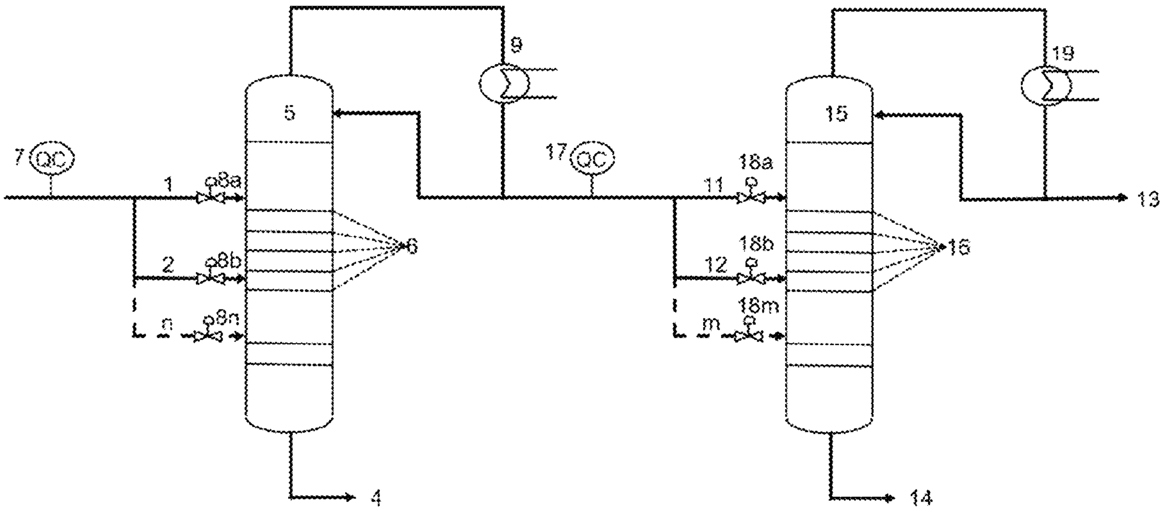
FIG. 2 shows a configuration in which the vapour stream from the first distillation column DK1 (5) can be directed into the distillation column DK2 (15) via conduit 11, conduit 12 or optionally an additional conduit m or via the corresponding inlets.

FIG. 2 shows a further embodiment of the invention that corresponds largely to the embodiment according to FIG. 1. The difference from FIG. 1. is that the vapour stream from the first distillation column DK1 (5) can be directed into the distillation column DK2 (15) via conduit 11, conduit 12 or optionally an additional conduit m or via the corresponding inlets. The dotted conduit m indicates that further inlets may be present. Which of these conduits should be chosen is determined by analysis of the raffinate 2 via the corresponding analysis unit QC (17). The feeding of the portion of the condensed vapour stream via one of the inlets (11, 12, m) is adjusted with the aid of valves (18*a*, 18*b*, 18*m*).

Figure 3:
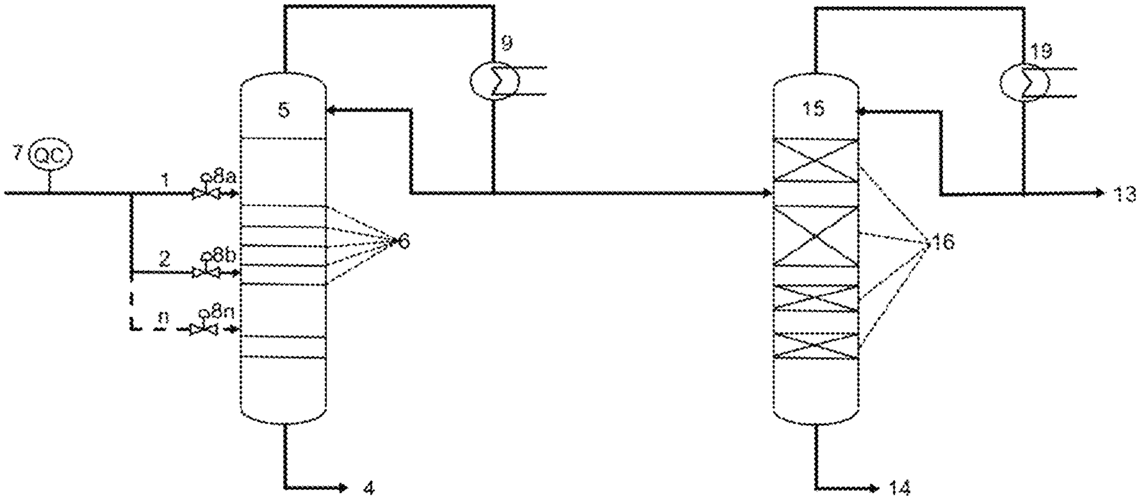
FIG. 3 shows a configuration in which internals (16) present in the second distillation column DK2 (15) are random packings or structured packings.

FIG. 3 shows a further embodiment of the invention that corresponds largely to the embodiment according to FIG. 1. The difference from FIG. 1 is that internals (16) present in the second distillation column DK2 (15) are random packings or structured packings.

Figure 4:
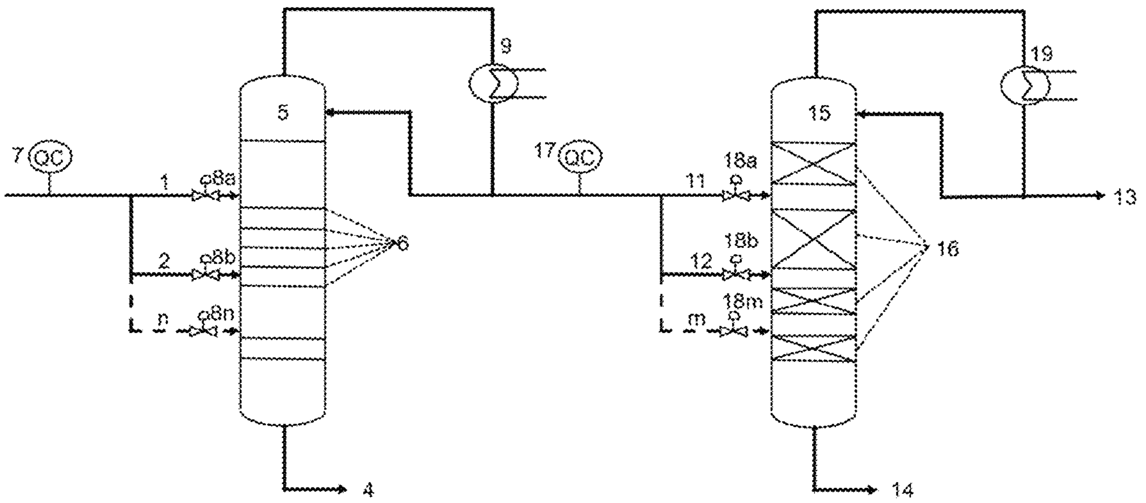
FIG. 4 shows a configuration in which internals (16) present in the second distillation column DK2 (15) are random packings or structured packings.

FIG. 4 shows a further embodiment of the invention that corresponds largely to the embodiment according to FIG. 2. The difference from FIG. 2 is that internals (16) present in the second distillation column DK2 (15) are random packings or structured packings.

Figure 5:
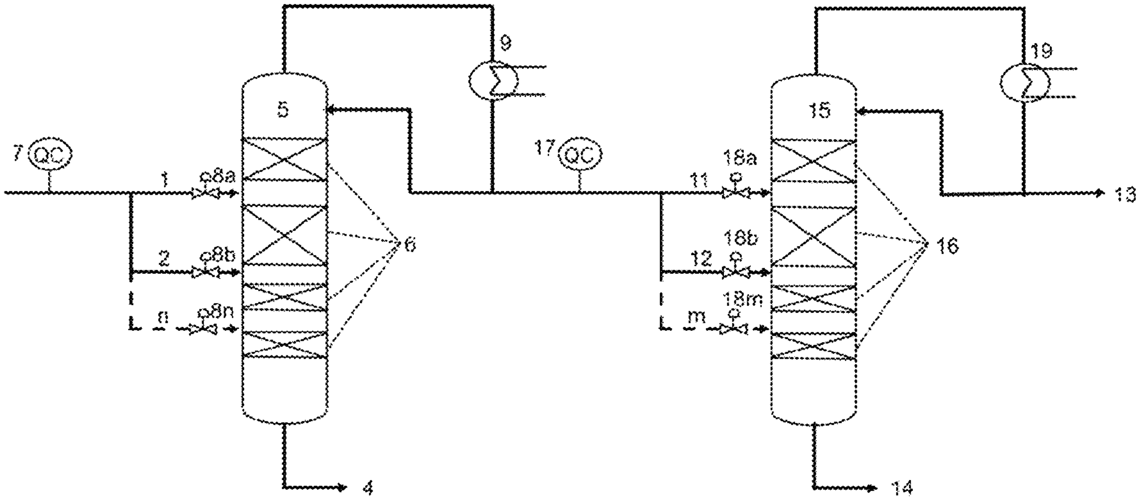
FIG. 5 shows a configuration in which internals (16) present in the first distillation column DK1 (5) are likewise random packings or structured packings.

FIG. 5 shows a further embodiment of the invention that corresponds largely to the embodiment according to FIG. 4. The difference from FIG. 4 is that internals (16) present in the first distillation column DK1 (5) are likewise random packings or structured packings.

Figure 6:
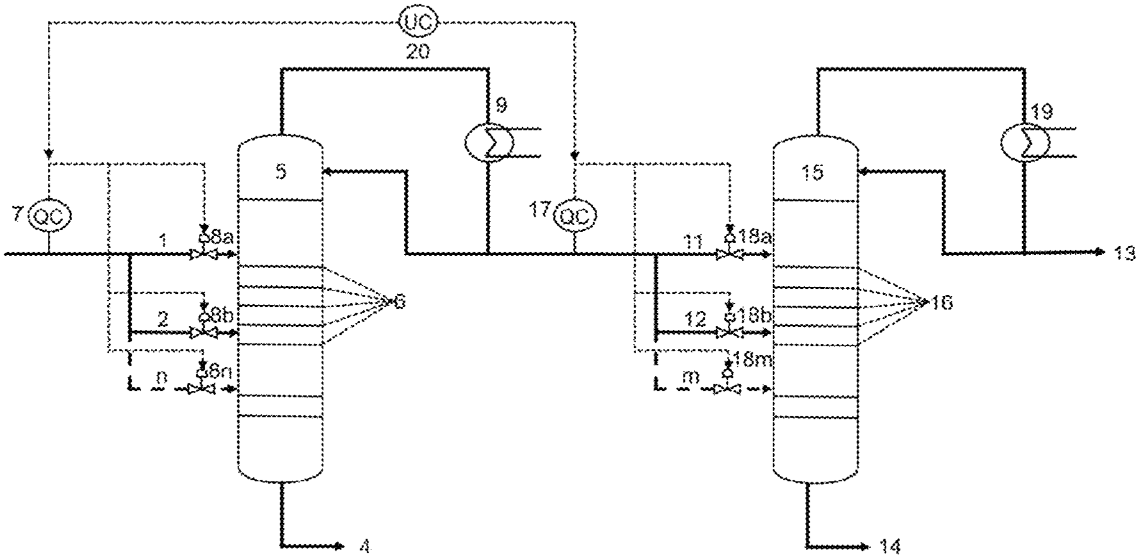
FIG. 6 shows a configuration in which the analysis units (7, 17) are connected to a control unit (UC) by means of which the analysis results are evaluated and the changeover to another inlet can be effected with the aid of the valves (8*a*, 8*b*, 8*n*, 18*a*, 18*b*, 18*m*).

FIG. 6 shows a further embodiment of the present invention that corresponds largely to the embodiment according to FIG. 2. The difference from FIG. 2 is that the analysis units (7, 17) are connected to a control unit (UC) by means of which the analysis results are evaluated and the changeover to another inlet can be effected with the aid of the valves (8*a*, 8*b*, 8*n*, 18*a*, 18*b*, 18*m*).

Figure 7:
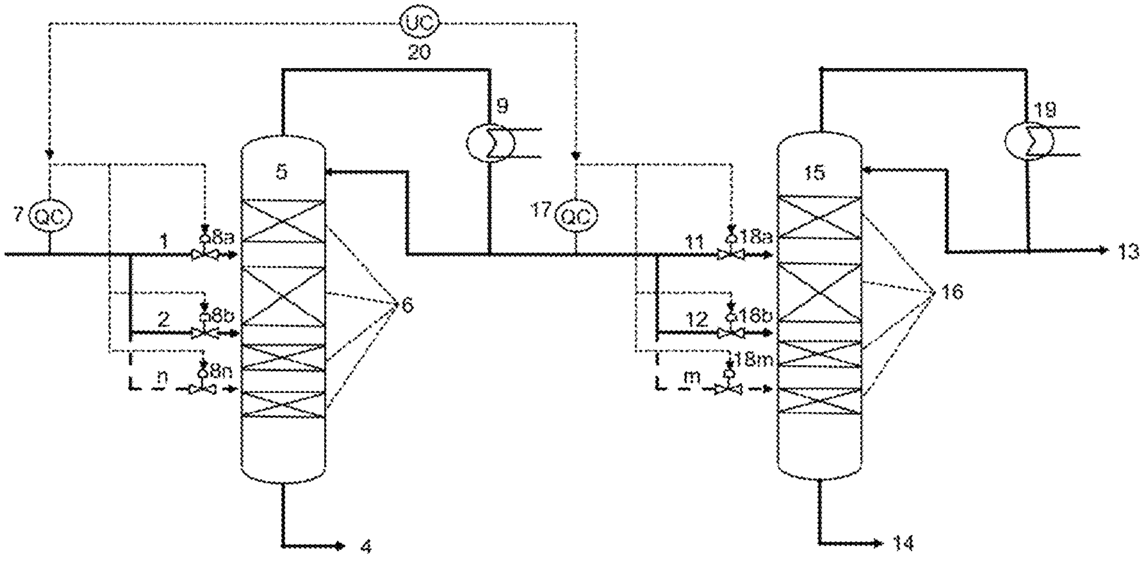
FIG. 7 shows a configuration in which internals (16) present in the second distillation column DK2 (15) are random packings or structured packings.

FIG. 7 shows a further embodiment of the invention that corresponds largely to the embodiment according to FIG. 6. The difference from FIG. 6 is that internals (16) present in the second distillation column DK2 (15) are random packings or structured packings.

Figure 8:
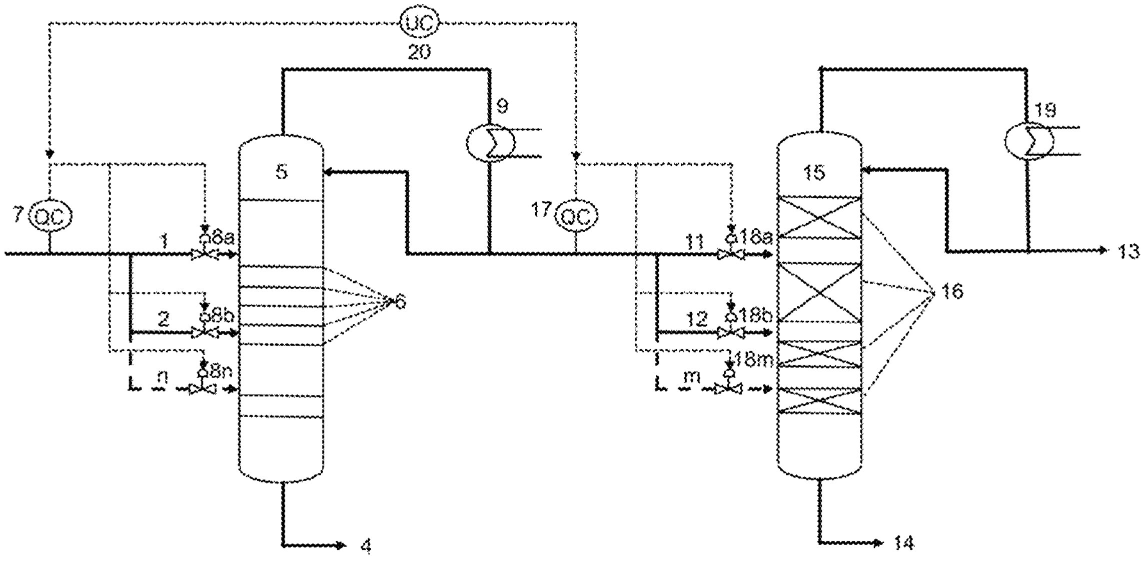
FIG. 8 shows a configuration in which internals (16) present in the first distillation column DK1 (5) are likewise random packings or structured packings.

FIG. 8 shows a further embodiment of the invention that corresponds largely to the embodiment according to FIG. 4. The difference from FIG. 7 is that internals (16) present in the first distillation column DK1 (5) are likewise random packings or structured packings.

Figure 9:
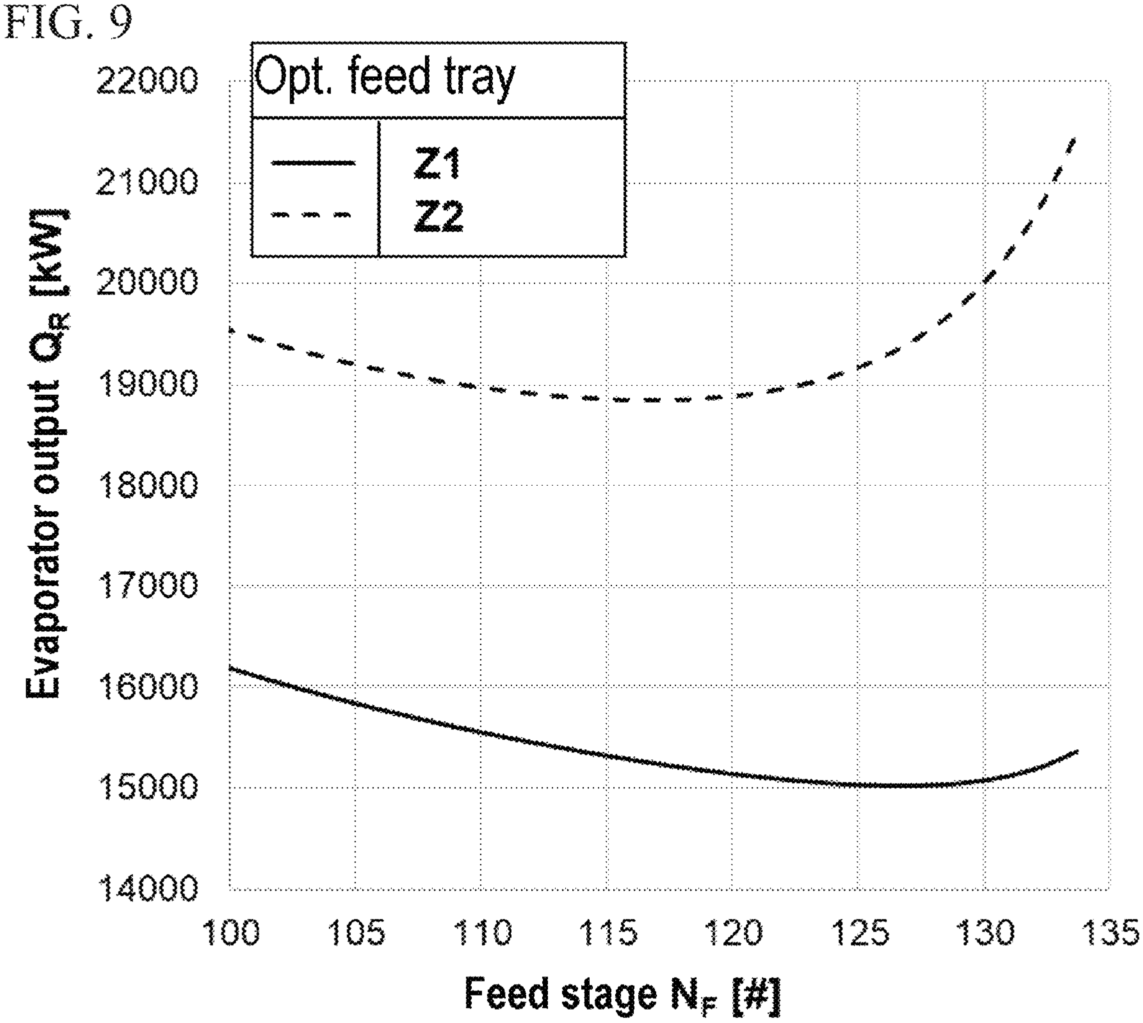
FIG. 9 shows a diagram in which the required evaporator output $Q_R$ is plotted as a function of the tray (here, feed stage $N_F$) for the two compositions Z1 and Z2.

FIG. 9 shows a diagram in which the required evaporator output $Q_R$ is plotted as a function of the tray (here, feed stage $N_F$) for the two compositions Z1 and Z2. Elucidations can be found in the example that follows.

Example

This example considers a column with which 1-butene and isobutane are separated overhead from a raffinate 2 stream. This example considers two different compositions (Z1 and Z2) of the raffinate 2 stream that are intended to take account, for example, of seasonal raw material fluctuations. Table 1 shows the different feed compositions.

TABLE 1

Raffinate 2 compositions

| | | Z1 x [wt %] | Z2 x [wt %] |
|---|---|---|---|
| i-butane | | 7.5 | 7.5 |
| 1-butene | | 45.5 | 35.5 |
| n-butane | | 22.5 | 32.5 |
| 2-butene | t-butene | 16 | 16 |
| | c-butene | 8.5 | 8.5 |

The calculations were conducted with Aspen Plus® Version 10 and an adapted physical data model based on operationally validated substance data. A column having 140 theoretical plates (200 trays with tray efficiency 0.7) was modelled. The n-butane content was kept constant at 800 ppm in the top. FIG. 5 shows the resulting diagram in which the required evaporator output $Q_R$ is plotted as a function of the tray (here, feed stage $N_F$) for the two compositions Z1 and Z2. The energy demand is at its lowest at the lowest point in the respective curve. Table 2 shows a sensitivity analysis that shows the correlation between the tray and the required amount of heat in megawatts (MW) in the evaporator (QR) as a function of the composition of the feed (Z1 and Z2). In the case of a high 1-butene content in the feed (Z1), it is advantageous to run the feed to the 126th plate. The evaporator requires 0.13 MW less than if the raffinate with composition Z1 is run to the 119th plate. For high n-butane contents in the feed, as in composition Z2, a greater total amount of heat is required. In addition, the optimal tray is different. While tray 126 is energetically advantageous in the case of composition Z1, tray 119 should be chosen in an energetically preferable manner in the case of composition Z2. Accordingly, a changeover of tray results in an energy saving of 0.49 MW. These energy savings result in a saving of $CO_2$ and operating costs.

TABLE 2

| Results of the sensitivity analysis | | |
|---|---|---|
| Plate | Z1 QR [MW] | Z2 QR [MW] |
| 119 | 15.15 | 18.87 |
| 126 | 15.02 | 19.36 |

The invention claimed is:

1. A process for distilling a raffinate 2 stream comprising 1-butene, 2-butene, n-butane, and isobutane, as feed stream in a separation unit comprising a first distillation column DK1 and a second distillation column DK2, wherein the first distillation column DK1 and the second distillation column DK2 each comprise a top at an upper end of a column and a bottom at a lower end of the column, the process comprising:

obtaining a vapor stream at the top of the first distillation column DK1 and at the top of the second distillation column DK2 and a bottom stream at the bottom of the first distillation column DK1 and at the bottom of the second distillation column DK2, feeding, to the second distillation column DK2, a portion of the vapor stream from the second distillation column DK2;

at least partly condensing the vapor streams from the first distillation column DK1 and the second distillation column DK2, and heating, with a condensation energy obtained from at least one of the vapour streams from the first distillation column DK1 or the second distillation column DK2, by vapour compression or by a heat pump, the first distillation column DK1 and/or the second distillation column DK2;

wherein at least the first distillation column DK1 has at least two different inlets for the feed stream, where the at least two different inlets, viewed from the top of the first distillation column DK1, are arranged one below another;

wherein the feed stream is analysed for its composition before being introduced; and wherein one of the at least two different inlets for a supply of the feed stream is chosen depending on a composition of the feed stream, further comprising:

feeding, from the first distillation column DK1, the hydrocarbon stream in the second distillation column DK2 through at least two different inlets, wherein the at least two different inlets, viewed from the top of distillation column DK2, are arranged one below another;

wherein the bottoms stream from the second distillation column DK2 is not recycled back to the first distillation column DK1.

2. The process according to claim 1, wherein the first distillation column DK1 comprises internals selected from the group consisting of random packings, structured packings and trays.

3. The process according to claim 2, wherein the internals within the first distillation column DK1, viewed from the top of the first distillation column DK1, are arranged one below another, and wherein the at least two different inlets are present at a height of different internals.

4. The process according to claim 1, wherein, during the process, a composition of the raffinate 2 stream changes and wherein the process further comprises switching over to another inlet.

5. The process according to claim 4, wherein the switching of the raffinate 2 stream to another inlet is automatic or manual.

6. The process according to claim 5, wherein the switching is made automatically and comprises evaluating the analysis results by a control unit, and, in the event that a value goes above or below a limit in the composition of the raffinate 2 stream, the switching to another inlet is made.

7. The process according to claim 1, wherein the analysing of the composition of the raffinate 2 stream comprises Raman spectroscopy or by gas chromatography.

8. The process according to claim 1, wherein the process is conducted continuously or in batchwise mode.

9. The process according to claim 1, wherein at least the first distillation column DK1 and the second distillation column DK2 is operated with reflux, and a reflux ratio is less than 1 to 100.

10. The process according to claim 1, wherein the composition of the raffinate 2 stream is analysed continuously throughout the process at predefined time intervals.

11. The process according to claim 1, wherein the second distillation column DK2 comprises internals selected from the group consisting of random packings, structured packings and trays.

12. The process according to claim 11, wherein the internals within DK2, viewed from the top of the distillation column, are arranged one below another, and the at least two inlets are present at a height of different internals.

13. The process according to claim 1, wherein the raffinate 2 stream consists essentially of 1-butene, 2-butene, n-butane, and isobutane.

14. The process according to claim 1, wherein the raffinate 2 stream contains less than 500 ppm of isobutene.

15. The process according to claim 1, wherein the raffinate 2 stream contains less than 500 ppm of polyunsaturated C4 hydrocarbons.

16. The process according to claim 1, further comprising withdrawal of at least one product stream comprising 1-butene at the bottom of distillation column DK2.

17. The process according to claim 16, wherein the product stream contains at least 99% by weight of 1-butene.

18. The process according to claim 1, wherein raffinate 2 is separated in distillation column DK1 into at least two streams, including a vapor stream BS1 that comprises at least 1-butene and isobutane and a bottom stream which comprises at least 1-butene and 2-butene.

* * * * *